United States Patent [19]

Shackelford

[11] 4,205,767

[45] Jun. 3, 1980

[54] CANNULA INJECTION DEVICE

[75] Inventor: Carl L. Shackelford, San Pablo, Calif.

[73] Assignee: Altex Scientific, Inc., Berkeley, Calif.

[21] Appl. No.: 920,002

[22] Filed: Jun. 28, 1978

[51] Int. Cl.² .............................................. B67D 5/06
[52] U.S. Cl. ................................. 222/542; 128/272.3;
    277/112; 277/125
[58] Field of Search ................... 222/542; 128/214.2,
    128/272.3, 763, 764; 277/125, 112

[56] References Cited

U.S. PATENT DOCUMENTS

| 3,035,616 | 5/1962 | Hamilton | 222/542 X |
| 3,072,415 | 1/1963 | Lombard et al. | 277/112 |
| 3,113,999 | 12/1963 | Heikkinen | 277/125 X |

FOREIGN PATENT DOCUMENTS 623492  6/1927  France ..................... 277/112

Primary Examiner—Joseph J. Rolla
Attorney, Agent, or Firm—Bielen and Peterson

[57] ABSTRACT

An injection device for use with a fluid transporting cannula and a female fitting for a liquid system. The cannula is surrounded by a first sleeve which in itself is surrounded by a second sleeve. The end portion of the second sleeve places within the female fitting. A first seal is formed about the opening in the base of the female fitting and a second seal is formed between the first sleeve and the outside of the cannula. A force producing element urges the end portion of the second sleeve toward the base of the female fitting.

8 Claims, 3 Drawing Figures

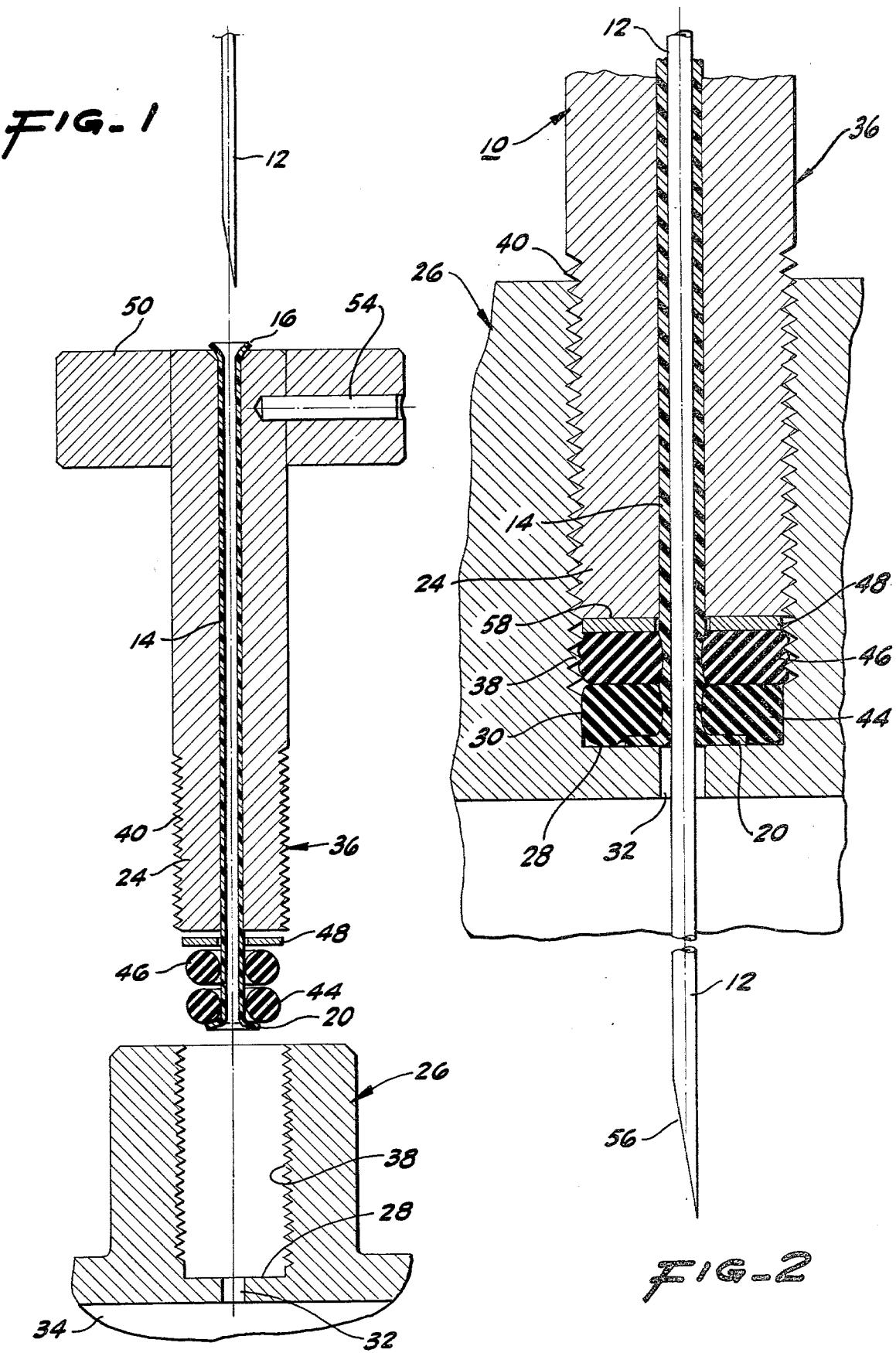

CANNULA INJECTION DEVICE

BACKGROUND OF THE INVENTION

The present invention relates to a novel cannula injection device for permitting access to a liquid system.

Gas and liquid chromatography systems often require the injection of unknown compounds into suitable eluding solvents. Prior methods of injecting liquid samples have employed septum injectors, plungers, and various sample injection valves having sample loops. All prior systems have encountered the problems of accurate measurement of the sample being injected as well as leakage problems associated with fluid systems under pressure. Also, prior injection devices tend to be cumbersome since they cannot be easily removed from the fluid system apparatus. It has been found that conventional syringes permit accurate gauging of the fluid samples being injected into a system. However, the problem of providing convenient access to the fluid system by the cannula without leakage problems usually associated therewith, still remains.

SUMMARY OF THE INVENTION

In accordance with the present invention a novel injection device for use with a fluid transporting cannula is provided. The device of the present invention is useable with a female fitting having a base, side portions, and an opening permitting access to the fluid system.

The device includes a first sleeve surrounding at least a portion of the cannula. The first sleeve may be deformable for resilience. A second sleeve surrounds at least a portion of the first resilient sleeve. The second sleeve may be relatively rigid in relation to the first sleeve. The second sleeve includes an end portion adapted for placement within the female fitting. In many cases the sides of the female fitting may be threaded such that a threaded end portion of the second sleeve threadingly engages the threaded inner portion of the female fitting.

First sealing means tightly closes the area about the opening in the base of the female fitting. Also, second sealing means squeezes the first sleeve around the cannula to prevent liquid from passing therebetween. The first sleeve may be formed with an end flange such that the flange serves as first sealing means herebefore described. The invention also includes means for forcing the end portion of the second sleeve toward the base of the female fitting. This forcing means generally causes the first and second sealing means to function.

Second sealing means may externalize in at least one deformable member which is interposed the base of the female fitting and the end portion of the second sleeve. The squeezing of the forcing means causes the deformable member to seal the first sleeve about the cannula exterior surface.

The first sleeve thus permits insertion of a cannula into the opening of the female fitting until initiation of the sealing mechanism by the forcing means. At this point the fluid from the fluid system cannot escape therefrom except through the interior of the cannula. The invention may also include means for rotating the second sleeve to effect the threading engagement of the end portion of the second sleeve and the female fitting, heretofore described.

It may be apparent that a novel and useful cannula injection device has been described.

It is therefore an object of the present invention to provide a novel and useful cannula injection device which permits the insertion of a cannula into a fluid system and prevents leakage from the fluid system outside the inside of the cannula itself.

It is another object of the present invention to provide a cannula injection device easily and efficiently usable in a relatively low pressure (generally below 1000 PSI) system.

It is another object of the present invention to provide a cannula injection device which may be constructed to be chemically inert in relation to the fluid system.

It is yet another object of the present invention to provide a cannula injection device which may be easily maintained and repaired.

The invention possesses other objects and advantages, especially as concerns particular features and characteristics thereof, which will become apparent as the specification continues.

BRIEF DESCRIPTION OF THE DRAWINGS

FIG. 1 is a partially broken sectional view of the device in its environment.

FIG. 2 is a partially broken, slightly exploded sectional view of the device and its environment.

FIG. 3 is a sectional view depicting the device while in use.

Various aspects of the present invention will evolve from the following detailed description of the preferred embodiments thereof which should be taken in conjunction with the hereabove described drawings.

DESCRIPTION OF THE PREFERRED EMBODIMENTS

The invention as a whole shown in the drawings as being represented by reference character 10. The device 10 is usable with a cannula 12 generally found in conjunction with a hyperdermic needle and syringe (not shown). Cannula 12 may be constructed of metallic material such as steel, aluminum, and the like. A first sleeve 14 is sized to accept cannula 12 such that sleeve 14 surrounds at least a portion of the cannula 12. It is desirable to have cannula 12 easily slip in and out of sleeve 14. One end portion 16 of sleeve 14 is funnel shaped to aid the insertion of cannula 12 within sleeve 14. The other end portion 18 of sleeve 14 forms into a flange 20, the purpose of which will be hereinafter described, FIG. 1.

A second sleeve 22 surrounds at least a portion of the first sleeve 14. Second sleeve 22 may be relatively rigid in relation to first sleeve 14. For example, the first sleeve 14 may be constructed of Teflon, or other fluorocarbon materials, while second sleeve 22 may be formed of stainless steel and the like. End portion 24 of second sleeve 22 may be placed within female fitting 26. It should be noted that female 26 includes a base 28, side portions 30, and an opening 32. Fitting 26, and in particular opening 32, lead into fluid system 34. It is anticipated that fluids 34 may be under pressures up to approximately 70 kilograms per square centimeter.

Means 36 forces end portion 24 of sleeve 22 toward the base 28 of female fitting 26. In the preferred embodiments means 36 embraces threaded portion 38 of side portions 30 within fitting 26 and threaded portion 40 of end portion 24 of sleeve 22. As may be apparent, threaded 38 portion 38 threadingly engages threaded portion 40 to force and portion 24 toward base 28.

The invention also has second sealing means 42 which seals first sleeve 14 to the exterior of cannula 12. Second sealing means is activated by forcing means 36. The embodiment shown in the drawings illustrates second sealing means 42 as including a pair of "O" rings 44 and 46 and a washer 48. It should be understood that other elements such as another washer (not shown) may be placed between end portion 24 and base 28 during threading engagement of threaded portions 38 and 40. "O" rings 44 and 46 may be constructed of deformable, or resilient elastomers such as buna-n, viton and the like.

Means 50 aids in the rotation of second sleeve 22 within female fitting 26. Means 50 includes gripping portion 52 secured to second sleeve 22 by fastening means 54.

In operation, FIG. 2, cannula 12 is inserted within first sleeve 14 such that the point 56 thereof extends sufficiently away from end portion 24. The user then places point 56 of cannula 12 to opening 32. Cannula 12 extends within fluid system 34 until the threaded portion 40 engages threaded portion 38. Means 50 is then rotated to provide forcing means 36, heretofore described. "O" rings 44 and 46 are squeezed between base 28 and end 58 of of end portion 24. Being thus confined between base 28 and 58 and side portions 30 of fitting 26, "O" rings 44 and 46 force the lower portion of first sleeve 14 into sealing engagement around cannula 12. At the same time, flange 20 is forced into sealing engagement with portion of base 28 surrounding opening 32. In essence fluid from fluid system 24 cannot escape along the exterior of cannula 12 and between threaded portions 38 and 40. The only access to fluid system 34 lies through the inside diameter of cannula 12. The samples of fluid system 34 may be withdrawn through cannula 12 or exotic chemicals may be injected through cannula 12 to fluid system 34.

While in the foregoing specification embodiments of the invention have been setforth in considerable detail for the purposes of making a complete disclosure of the invention, it will be apparent to those of ordinary skill in the art that numerous changes may be made in such details without departing from the spirt and principals of the invention.

What is claimed is:

1. An injection device for use with a fluid transporting cannula and a female fitting having a base, side portions, and an opening permitting access to a fluid system comprising:
   a. a first sleeve surrounding at least a portion of the cannula, said first sleeve having a flanged end portion;
   b. a second sleeve surrounding at least a portion of said first sleeve, said second sleeve having an end portion for placement within the female fitting;
   c. first sealing means for sealing the area about the opening in the base of the female fitting, said first sealing means including means for pressing said flanged end portion of said first sleeve into sealing engagement about the opening in the base of the female fitting;
   d. means for forcing said end portion of said second sleeve toward the base of the female fitting; and
   e. second sealing means for sealing said first sleeve around the cannula upon the activation of said forcing means, said second sealing means including at least one deformable member being interposed the base of the female fitting and said end portion of said second sleeve.

2. The injection device of claim 1 in which said first sleeve is deformable.

3. The injection device of claim 2 in which said means for forcing said end portion of said second sleeve toward the base of the female fitting comprises a threaded part of said end portion of said second sleeve threadingly engaging a threaded portion of the sides of the female fitting.

4. The injection device of claim 1 in which said means for pressing said flanged end portion of said first sleeve comprises said means for forcing said end portion of said second sleeve toward the base of the female fitting.

5. The injection device of claim 4 in which said at least one deformable member comprises an "O" ring.

6. The injection device of claim 5 which additionally comprises means for rotating said second sleeve in relation to the female member.

7. The injection device of claim 4 in which said first sleeve is deformable.

8. The injection device of claim 7 in which said means for forcing said end portion of said second sleeve toward the base of the female fitting comprises a threaded part of said end portion of said second sleeve threadingly engaging a threaded portion of the sides of the female fitting.

* * * * *